United States Patent
Dai et al.

(10) Patent No.: US 11,359,012 B1
(45) Date of Patent: Jun. 14, 2022

(54) SPECIFIC CHIMERIC ANTIGEN RECEPTOR CELLS TARGETING HUMAN CLDN18A2, PREPARATION METHOD AND APPLICATION THEREOF

(71) Applicant: NANJING KAEDI BIOTHERAPEUTICS LTD., Nanjing (CN)

(72) Inventors: Hongjiu Dai, Nanjing (CN); Hui Xu, Nanjing (CN); Jingjing Zhu, Nanjing (CN); Mengyao Wang, Nanjing (CN)

(73) Assignee: NANJING KAEDI BIOTHERAPEUTICS LTD., Nanjing (CN)

( * ) Notice: Subject to any disclaimer, the term of this patent is extended or adjusted under 35 U.S.C. 154(b) by 0 days.

(21) Appl. No.: 17/458,612

(22) Filed: Aug. 27, 2021

(51) Int. Cl.
| | |
|---|---|
| *C07K 16/28* | (2006.01) |
| *C12N 5/0783* | (2010.01) |
| *C07K 14/705* | (2006.01) |
| *C07K 14/725* | (2006.01) |
| *A61P 35/00* | (2006.01) |
| *C12N 15/86* | (2006.01) |
| *A61K 39/00* | (2006.01) |
| *A61K 38/00* | (2006.01) |

(52) U.S. Cl.
CPC .............. *C07K 16/28* (2013.01); *A61P 35/00* (2018.01); *C07K 14/7051* (2013.01); *C07K 14/70517* (2013.01); *C07K 14/70578* (2013.01); *C12N 5/0636* (2013.01); *C12N 15/86* (2013.01); *A61K 38/00* (2013.01); *A61K 2039/505* (2013.01); *A61K 2039/5156* (2013.01); *A61K 2039/5158* (2013.01); *C07K 2317/569* (2013.01); *C07K 2317/622* (2013.01); *C07K 2319/02* (2013.01); *C07K 2319/03* (2013.01); *C07K 2319/30* (2013.01); *C07K 2319/33* (2013.01); *C12N 2510/00* (2013.01); *C12N 2740/15043* (2013.01); *C12N 2740/15071* (2013.01)

(58) Field of Classification Search
CPC .... C07K 16/28; C07K 14/7051; A61K 38/00; A61K 2039/505; A61P 35/00
See application file for complete search history.

(56) References Cited

U.S. PATENT DOCUMENTS

| | | |
|---|---|---|
| 10,377,822 B2 | 8/2019 | Wang et al. |
| 2019/0321404 A1 | 10/2019 | Fan et al. |
| 2020/0062843 A1 | 2/2020 | Wang et al. |
| 2020/0078399 A1 | 3/2020 | Fan et al. |
| 2020/0318067 A1 | 10/2020 | Gilham et al. |

FOREIGN PATENT DOCUMENTS

WO     2018087557 A1     5/2018

OTHER PUBLICATIONS

Ugur Sahin, et al., Claudin-18 SpliceVariant 2 is a Pan-Cancer Target Suitable for Therapeutic Antibody Development, Clin Cancer Res, 2008, pp. 7624-7634, 14(23).

*Primary Examiner* — Ruixiang Li

(74) *Attorney, Agent, or Firm* — Bayramoglu Law Offices LLC

(57) ABSTRACT

A chimeric antigen receptor (CAR) cell specifically targeting human Claudin18.2 (CLDN18A2), a preparation method and an application thereof are provided. The extracellular binding region of the CAR includes a protein specifically recognizing CLDN18A2 that has any one of the amino acid sequences as shown in SEQ ID NOS: 2-5 or any one of the amino acid sequences of the variants having 70%-99% identity with the amino acid sequences shown by the SEQ ID NOS: 2-5. The immune effector cell modified by the CAR can be used to treat tumors.

7 Claims, 6 Drawing Sheets

Specification includes a Sequence Listing.

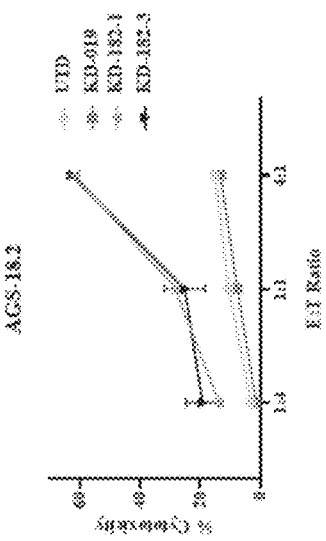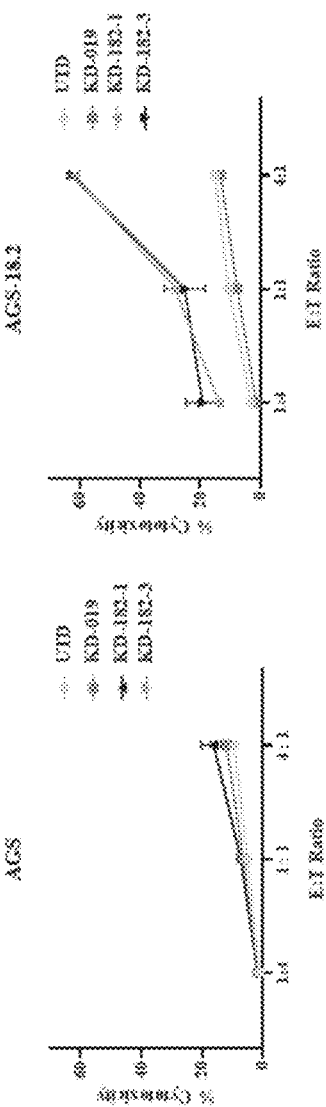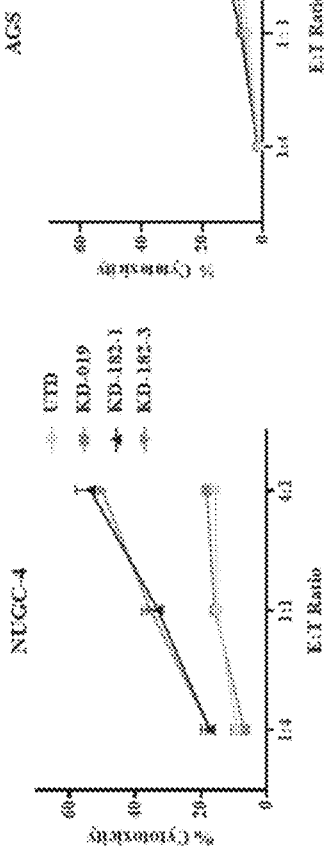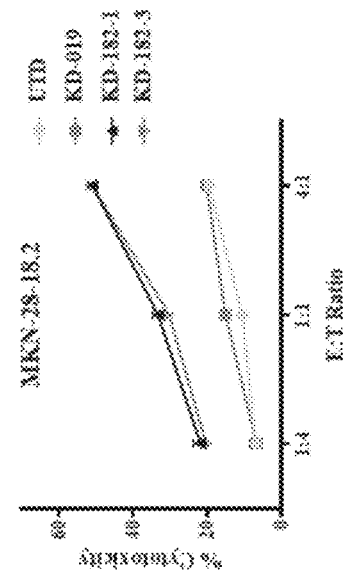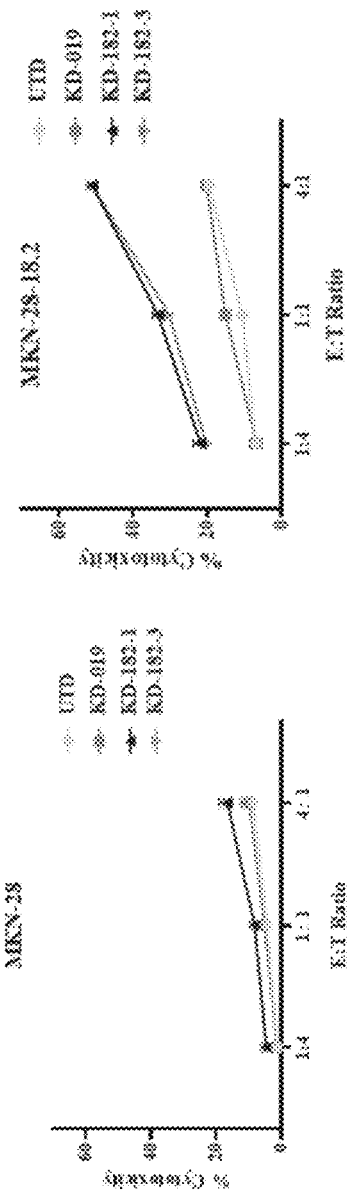

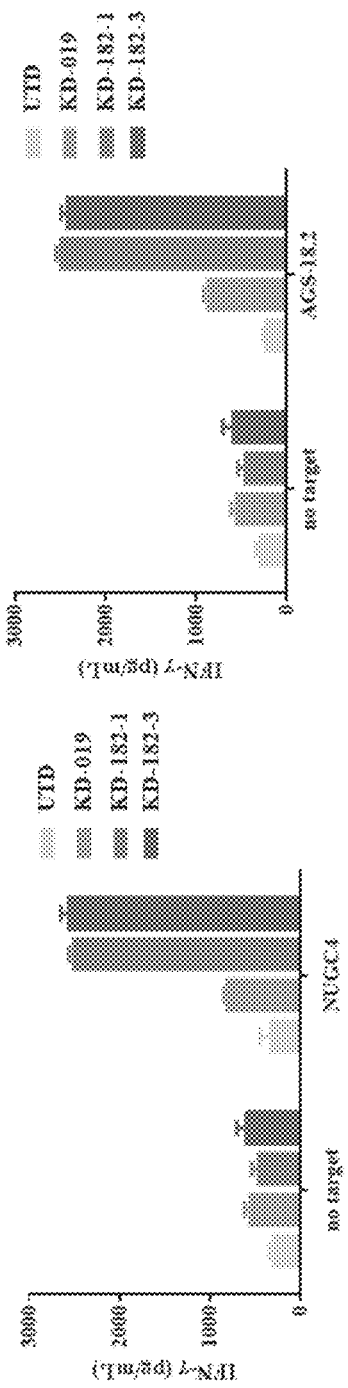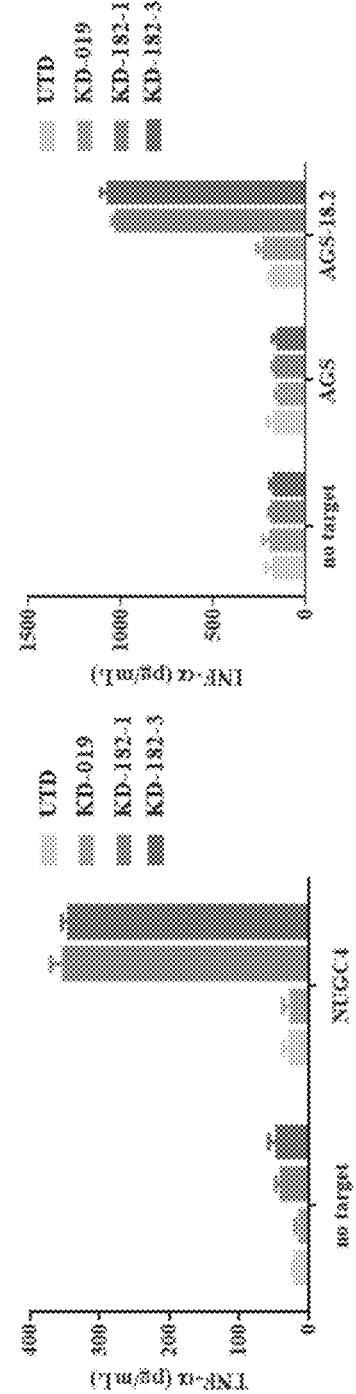
FIG. 5A  FIG. 5B
FIG. 5C  FIG. 5D

AGS-18.2

SPECIFIC CHIMERIC ANTIGEN RECEPTOR CELLS TARGETING HUMAN CLDN18A2, PREPARATION METHOD AND APPLICATION THEREOF

SEQUENCE LISTING

The instant application contains a Sequence Listing which has been submitted in ASCII format via EFS-Web and is hereby incorporated by reference in its entirety. The ASCII copy is named GBKDYL001_Sequence_Listing.txt, created on Jul. 26, 2021 and is 38,606 bytes in size.

TECHNICAL FIELD

The invention belongs to the field of cell therapy for tumors, and particularly relates to an immune effector cell targeting CLDN18A2, preparation method and application thereof.

BACKGROUND

With the rapid development of biotechnology, immune cell therapy has become the fourth major therapy in the field of cancer treatment.

Cancer immunotherapy mainly includes adoptive cell therapy, cytokines, monoclonal antibodies (mAbs), tumor vaccines, immunology checkpoint block therapy and so on. Chimeric antigen receptor-T (CAR-T) cell immunotherapy is a form of adoptive cell therapy and has provided a dramatically advanced breakthrough as one of the most promising cancer immunotherapies.

CAR-T cells, as a rapidly emerging immunotherapeutic modality, are T cells that are genetically engineered to express an antigen-specific receptor that can recognize a target in a non-MHC restricted manner. This therapy has shown remarkable efficacy in the treatment of acute leukemia and non-Hodgkins lymphoma, and is considered to be one of the most promising cancer treatment modalities.

Trials of CAR-T cells in solid tumors followed soon after those in hematologic cancers. However, the application of CAR-T immunotherapy in solid tumors has many challenges, including immunological toxicity caused by sustained intense activation of the CAR-T cells resulting in a macrophage activation syndrome (MAS) and "On-target off-tumor" toxicity i.e., recognition of the target antigen on normal tissues. It is crucial to choose appropriate antigenic targets to generate high-efficiency CAR-T cells which eliminate tumor cells with minimum toxicity.

In recent years, studies have shown that Claudin proteins are the most crucial components of tight junctions, and play an essential role in maintaining cell polarity, regulating cell permeability and the intercellular ion. There have been 27 members of the family discovered so far and CLDN18A2 is one of the members which is becoming a promising antigen. CLDN18A2 is expressed exclusively on short-lived differentiated gastric epithelial cells in normal tissues and highly expressed on solid tumors such as gastric, pancreas, ovary, gallbladder, and lung adenocarcinoma (Sahin et al. Clinical Cancer Research (2008)). In addition, the exposed extracellular structure of CLDN18A2 allows for antibody binding, which makes it an ideal therapeutic target. Thus, CLDN18A2 is an ideal tumor antigen target of immunotherapy.

SUMMARY OF THE INVENTION

The purpose of the present invention is to provide an immune effector cell targeting human CLDN18A2 and the preparation method and application thereof.

In a first aspect, the present invention provides a specific chimeric antigen receptor expressed on the surface of an immune effector cell, wherein the chimeric antigen receptor comprises a sequentially connected extracellular binding region, a transmembrane region and an intracellular signal region, wherein the extracellular binding region comprises a protein which specifically recognizes human CLDN18A2.

In one preferred embodiment, the chimeric antigen receptor which specifically recognizes human CLDN18A2 comprises any one of the amino acid sequences of SEQ ID NOS: 2-5, or comprises any one of the amino acid sequences of the variants having 70%-99% identity with the amino acid sequences shown by the SEQ ID NOS: 2-5.

In some embodiments, the protein specifically recognizing human CLDN18A2 is an antibody or a ligand; preferably, the antibody is a single-chain antibody or single-domain antibody.

In a second aspect, this application provides a chimeric antigen receptor system comprising:
(i) a receptor component comprising the guiding peptide, an antigen binding domain, a transmembrane domain; and (ii) an intracellular signaling component comprising one or more of the following intracellular domains: CD28 intracellular domain, 4-1BB intracellular domain, OX40 intracellular domain and CD3 zeta intracellular domain.

In some embodiments, the specific chimeric antigen receptor also comprises a hinge region.

In some preferred embodiments, the chimeric antigen receptor comprises an extracellular binding domain, a transmembrane domain, and an intracellular signaling domain connected in the following sequences:

In one embodiment, the leader sequence is selected from SEQ ID NO: 1.

In some embodiments, the amino acid sequence of human CD8 in the hinge region is selected from SEQ ID NO: 6.

In some embodiments, the amino acid sequence of human CD8 in the transmembrane domain is selected from SEQ ID NO: 7.

In some embodiments, the human CD28 in the transmembrane domain is selected from SEQ ID NO: 8.

In some embodiments, the human 4-1BB intracellular domain is selected from SEQ ID NO: 9.

In some embodiments, the human CD28 intracellular domain is selected from SEQ ID NO: 10.

In some embodiments, the human OX40 intracellular domain is selected from SEQ ID NO: 11.

In some embodiments, the CD3 zeta intracellular domain is selected from SEQ ID NO: 12.

In another preferred embodiment, the chimeric antigen receptor comprises any one of the amino acid sequences of SEQ ID NOS: 13-16.

In a third aspect, this invention provides the nucleic acid encoding the chimeric antigen receptor.

In some embodiments, the nucleic acid encoding the chimeric antigen receptor comprises any one of the nucleotide sequences of SEQ ID NOS: 17-20.

In a fourth aspect, this application provides a vector comprising a nucleic acid sequence according to the third aspect of the invention.

The vector may, for example, be a retroviral vector or a lentiviral vector or a transposon.

In a fifth aspect, this application provides a recombinant virus which expressing a chimeric antigen receptor specifically targeting human CLDN18A2 as according to the second aspect of the invention.

In a sixth aspect, this application provides a cell which expresses a receptor component and a signaling component as defined in the second aspect of the invention.

In some embodiment, the cell may comprise a nucleic acid according to the third aspect of the invention or a vector according to the fourth aspect of the invention.

The cell may be an immune cell such as a T cell, macrophage, human embryonic stem cells or an NK cell.

In a seventh aspect, there is provided a method of preparing a genetically modified immune effector cell targeting CLDN18A2.

In an eighth aspect, there is provided a pharmaceutical composition comprising a plurality of cells according to the sixth aspect of the invention.

In a ninth aspect, the application provides a kit for the treatment or prevention of a disease that contains an immune response cell described in the sixth aspect or a nucleic acid described in the third aspect.

In a tenth aspect, there is provided a method for making a cell according to the sixth aspect of the invention, which comprises the step of introducing a nucleic acid sequence according to the third aspect of the invention, or a vector according to the fourth aspect of the invention, or a kit according to the seventh aspect of the invention.

In some embodiment, the use of the genetically modified immune effector cells for preparation of a medicine for suppressing tumor, wherein the tumor is CLDN18A2 positive.

In some embodiment, the CLDN18A2 positive cancers include gastric cancer, pancreatic cancer, liver cancer, brain cancer, prostate cancer, lymphoma, leukemia, colon cancer, lung cancer, or breast cancer.

BRIEF DESCRIPTION OF THE DRAWINGS

FIGS. 3A-3C depict the results of the expression of CAR molecules detected by flow cytometry in embodiment 4, wherein FIG. 3A shows a blank control which means T cells without infection with virus, FIG. 3B and FIG. 3C show CAR-T cells targeting CLDN18A2.

FIGS. 4A-4E depict the cytotoxicity of KD-182-1 and KD-182-3 CAR-T cells on different target cells in embodiment 5. Primary human T cells transduced with the indicated lentivirus were co-incubated with the five gastric cancer cell lines NUGC-4 cells (FIG. 4A), AGS cells (FIG. 4B), AGS-18.2 cells (FIG. 4C), MKN-28 cells (FIG. 4D), and MKN-28-18.2 cells (FIG. 4E) at varying E: T ratios for 24 hours, respectively.

FIGS. 5A-5D show the results of cytokine release in the supernatant by KD-182-1 and KD-182-3 CAR-T cells when cocultured with NUGC-4, or AGS-18.2 cells; IFN-γ (FIGS. 5A and 5B) and TNF-α (FIGS. 5C and 5D) were detected in the supernatant collected after the culture in embodiment 6.

FIGS. 8A-8D depict the on-target off-tumor toxicities of both KD-182-1 and KD-182-3 CAR-T cells in embodiment 9, wherein FIG. 8A shows toxicological test results, FIG. 8B shows the test results of a safe tolerance dose experiment, and FIG. 8C and FIG. 8D show the respective cell viability corresponding to FIGS. 8A and 8B.

DETAILED DESCRIPTION OF THE EMBODIMENTS

Figure 1:
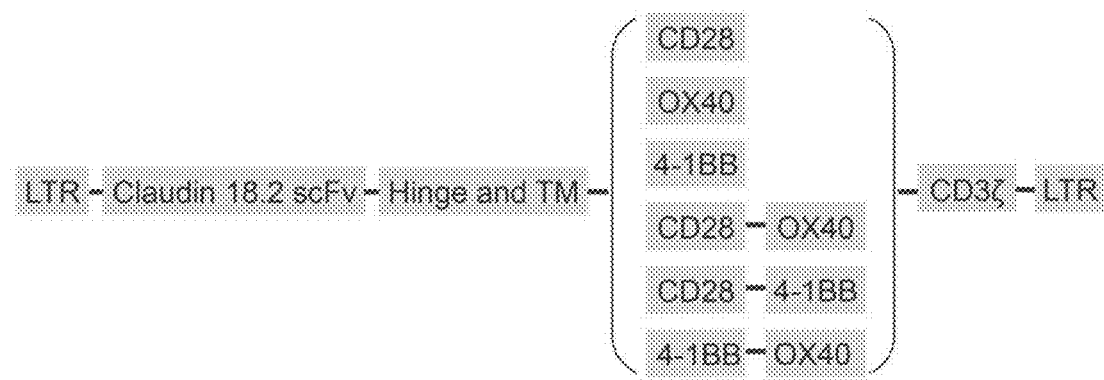
FIG. 1 is a schematic diagram of the connection sequences of each part of the chimeric antigen receptor in embodiment 2.

The term "variant" is modified by the maternal structure with the same or similar biological functions and properties, such as those having the same target binding function with the maternal structure. As a particular example, functional variants can be obtained from one or more places in the matrix.

The term "single-chain fragment variable (scFv)" as used herein refers to an antibody fragment defined as follows. It is a recombinant protein comprising a light chain variable region (VL) and a heavy chain variable region (VH) connected by a linker, and the linker associates the two domains by which an antigen binding site is finally formed.

The term "homology" refers to the amino group of the target amino sequence or the target nucleotide sequence matches with the reference sequence with a high proportion homology of acid or nucleotides. The homology in this application can be produced using standard software such as BLAST or FAST.

The term of chimeric antigen receptor (CAR) comprises the guiding peptide, extracellular target recognition domain, transmembrane domain and intracellular domain.

The term "recognition" refers to the selective combination of targets.

The term "specific combination" or "specific targeting" is used in this application which means that peptides or their fragments recognize and bind to the target molecules, such as peptides, but it basically does not recognize the binding of other molecules.

The term "vector" refers to any genetic element, such as plasmid, phage, transposon, chromosome, viruses, virus particles, which can be duplicated under appropriate control elements, and transfers gene sequence to the target cell. Therefore, the term comprises cloning and expression vectors, as well as viral vectors and plasmid.

The term "expression vector" refers to a recombinant nucleic acid sequence, that is, recombinant DNA molecule, which comprises the coding sequence and nucleic acids sequence necessary for expressing the coding sequences in specific host organisms. The nucleic acid sequences necessary for expression in prokaryotes typically comprise promoters, operon (optional) and ribosomal binding sites are usually accompanied by other sequences whereas eukaryotic cells utilize promoters, enhancers, terminator and polyadenine acidification signal.

The term "immune response cell" used in this application is the cell or its progenitor or its progeny cells that play an important role in the immune response.

The term "isolation cells" refers to the immune cells that are isolated from the molecules and/or cell components of natural cells mixture.

EXAMPLES

The embodiments of the present invention are further described below with reference to specific examples, but the invention is not limited to the scope of the invention.

The materials and reagents used in the following embodiments can be acquired from commercial companies without special explanation.

Example 1. Construction of Lentiviral Plasmids (KD-182-1, KD-182-2, KD-182-3 and KD-182-4 Lentiviral Vectors) Expressing Chimeric Antigen Receptor Proteins Encoded by the Nucleic Acids of the Present Invention The overall design is as follows:

Firstly, by repeatedly researching and analyzing, the inventors identified several scFv antibodies recognizing human CLDN18A2 protein, and their amino acid sequences are shown as SEQ ID NOS: 2-5.

Secondly, a chimeric antigen receptor specifically targeting human CLDN18A2 was constructed.

The corresponding nucleotide sequences comprise of scFv antibody recognizing human CLDN18A2, CD8 hinge region, CD8 transmembrane region, 4-1BB intracellular structure domain, CD3 zeta domain structure in series in turn (FIG. 1).

Table 1 shows the vectors constructed by using different nucleotide sequences targeting human CLDN18A2, and the corresponding CAR-T cells obtained according to the following methods. The results showed that there was no significant difference in CAR expression among the four groups, and two sequences were selected for subsequent efficacy verification.

| Samples | Amino acid sequence of CLDN18A2 single chain | Amino acid sequence of chimeric antigen receptor protein | CAR expression |
|---------|---------|---------|---------|
| KD-182-1 | SEQ ID NO: 2 | SEQ ID NO: 13 | 75.7% |
| KD-182-2 | SEQ ID NO: 3 | SEQ ID NO: 14 | 76.5% |
| KD-182-3 | SEQ ID NO: 4 | SEQ ID NO: 15 | 69% |
| KD-182-4 | SEQ ID NO: 5 | SEQ ID NO: 16 | 76.2% |

Third, construction of Lentiviral Plasmids expressing chimeric antigen receptor molecule specifically targeting human CLDN18A2.

The invention selected four sequences in step 1, which are KD-182-1 (SEQ TD NO: 17), KD-182-2 (SEQ ID NO: 18), KD-182-3 (SEQ ID NO: 19) and KD-182-4 (SEQ ID NO: 20). From the amino end to the carboxyl end, by the guidance of peptide amino acid sequence (SEQ ID NO: 1), the selected sequences have amino acid sequence of protein specifically recognizing human CLDN18A2 (SEQ ID NOS: 2-5), amino acid sequence of CD8 hinge region (SEQ ID NO: 6), amino acid sequence of human CD8 transmembrane area (SEQ ID NO: 7), 4-1BB intracellular structure domain of the amino acid sequence (SEQ ID NO: 9), and human CD3 zeta domain structure of amino acid sequence (SEQ ID NO: 12) in series in turn.

The whole gene synthesis specifically targeted the nucleotide sequence of the chimeric antigen receptor molecule of human CLDN18A2 (SEQ ID NOS: 17-20), and cloned into the lentiviral vector Lentigue-Purovia (Addgene, USA) to construct a full-length CAR sequence expression frame with a single coding frame, and an EF1a promoter was inserted in front of the CAR sequences.

The splicing conditions were as follows:

5 μL ligation product and 50 μL receptive cells (Stbl3, purchased from Invitrogen, USA) were added in a tube, incubated on ice for 30 min, 42° C. for 45 s, on ice for 2 min, then 500 μL non-anti-LB liquid medium was added, and shaken at 37° C., 200 rpm for 40 min. Finally, the suspension was coated on LB solid medium which has ampicillin, and the plates were incubated for 24 h at 37° C. When the single colony appearing, five moderately sized colonies were selected to extract plasmids and sent to the commercial company for sequencing. The right sequence will prove the plasmid expressing chimeric antigen receptor specifically targeting human CLDN18A2 is obtained.

Extraction and purification of chimeric antigen receptor expressing plasmid (KD-182-1, KD-182-2, KD-182-3 and KD-182-4 lentiviral vectors) specifically targeting human CLDN18A2 by QIAGEN Plasmid Midi Kits (Qiagen AG, article No. 12143).

Example 2. Virus Packaging

Packaging lentivirus by plasmid transfection of HEK293T. The transfection steps were as follows: the lentiviral plasmids which express the chimeric antigen receptor specifically targeting human CLDN18A2 obtained from Example 1 were co-transfected into HEK293T cells with the packaging plasmids pMDLg/pRRE, pRSV-Rev and pMD2.G (Addgene, USA) at a specific ratio. Medium (purchased from Life Technologies) was replaced 6 hours after transfection, and the supernatant which are rich in virus particles are then collected after 48 hours and 72 hours respectively. Finally, a 0.45 μm filter (purchased from Millipore Company) was used to filter and collect the virus, and centrifuged at 25,000 rpm, 4° C. for 2 hours, and the centrifuged supernatant was discarded. The precipitate obtained by centrifugation was resuspended with stock solution which carrying a lentiviral vector expressing a chimeric antigen receptor specifically targeting human CLDN18A2 (referred to as KD-182-1, KD-182-2, KD-182-3 and KD-182-4 lentivirus).

Example 3. Isolation and Culture of T Cells

Human peripheral blood mononuclear cells were obtained from healthy human peripheral blood through density gradient centrifugation method. T cells were obtained from peripheral blood mononuclear cells by negative sorting method with RosetteSep™ Human T Cell Enrichment Cocktail (purchased from Stem Cell Technologies), and the sorted cells were subjected to flow cytometry to determine the purity of the T cells.

Figure 2:
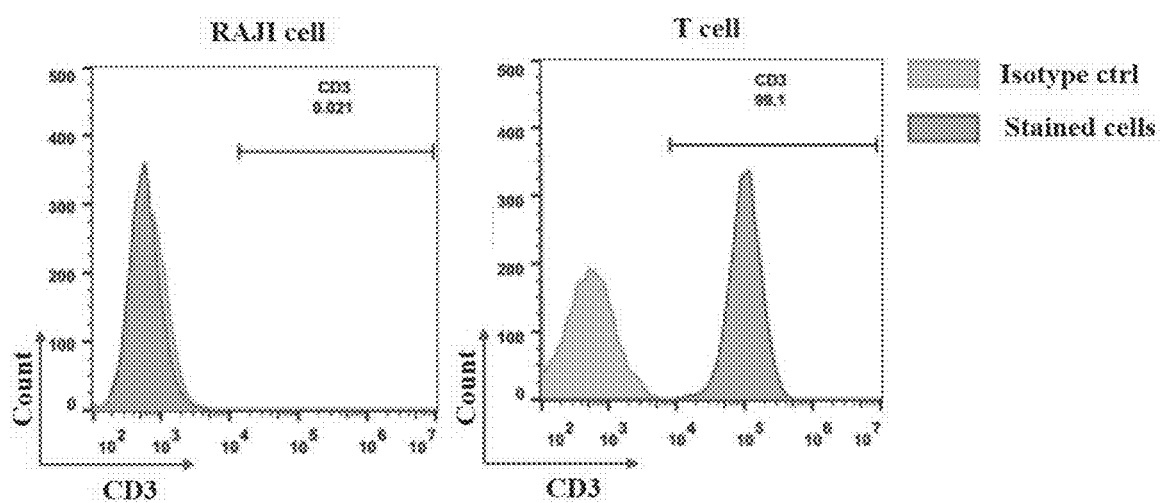
FIG. 2 depicts the result of T cell purity analyzed by flow cytometry in embodiment 3.

Culture medium (purchased from Life Technologies) was added at a density of about $(1-3) \times 10^6$/ml for culturing, and magnetic beads (Invitrogen company) coated with both anti-CD3 and CD28 antibodies, at 3: 1 cell-magnetic bead ratio, and recombinant human IL-2 with a final concentration of 100 U/ml were added to stimulate and culture for 48 h. As shown in FIG. 2, the purity of T cell was 99.1%.

Example 4. Recombinant Lentivirus Infection of T Cells

Figures 3A, 3B, 3C:
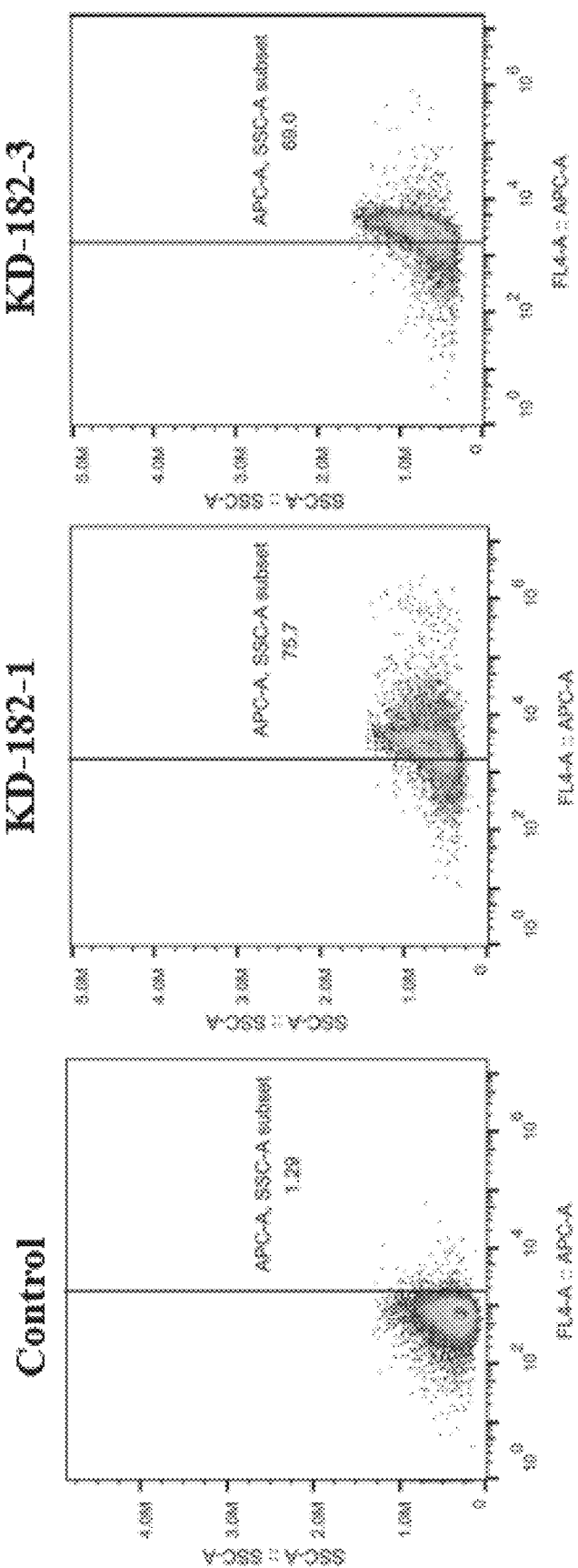

First, CD3+ T cells obtained from Example 3 were inoculated into a 24-well plate at the inoculation concentration of $1 \times 10^5$ cells/mL and incubated at 37° C., 5% $CO_2$ for 24 hours. Then the recombinant lentivirus from Example 2 were used to infect the T cells at MOI=1-10. After 48 hours, KD-182-1, KD-182-2, KD-182-3 and KD-182-4 CAR were detected in 75.7%, 76.5%, 69% and 76.2% of the T cells, respectively (FIGS. 3A-3C and Table 1).

Example 5. In Vitro Toxicity Effect Assay for Both KD-182-1 and KD-182-3 CAR-T Cells First, the effector cells (KD-019, KD-182-1 and KD-182-3 CAR-T cells) were prepared according to the method of Example 4 and were inoculated 72 hours after infection. The antitumor activity of CAR-T cells was evaluated using a Cell-Mediated Cytotoxicity Fluorometric Assay Kit (BioVision, USA). Briefly, carboxyfluorescein succinimidyl ester (CFSE)-stained target cells were seeded into 96-wells at a density of $4\times10^4$ cells/well. Subsequently, effector cells were added to each well to ensure an effector to target (E:T) ratios of 1:4, 1:1, and 4:1. After 24 h of co-culture, the tumor cells were collected, and dead cells were stained with 7-aminoactinomycin (7-AAD) and quantified by flow cytometry. KD-182-1 and KD-182-3 CAR-T cells could efficiently lyse NUGC-4, MKN-28-18.2 and AGS-18.2 cells, but not the CLDN18A2-negative AGS and MKN-28 cell line (less than 30-40%). In contrast, CD19 CAR-T cells failed to initiate the specific lysis of these cell lines (FIGS. 4A-4E). Besides, KD-182-1 and KD-182-3 CAR-T cells showed no significant difference in killing target cells.

Example 6. Cytokine Secretion Assay for Both KD-182-1 and KD-182-3 CAR-T Cells

First, the effector cells (KD-019, KD-182-1 and KD-182-3 CAR-T cells) were prepared according to the method of Example 4 and were inoculated 72 hours after infection. The target cells were seeded into 96-wells at a density of $4\times10^4$ cells/well. Subsequently, effector cells were added to each well to ensure an effector to target (E:T) ratios of 1:4, 1:1, and 4:1. After 24 h of co-culture, and the medium supernatant was assessed for the levels of cytokine secretion using Human IFN-γ ELISA Kit II (purchased from BD, No. 550612) and Human TNF-α ELISA Kit II (purchased from BD, No. 550610). As shown in FIGS. 5A-5D, greater amounts of TNF-α and IFN-γ were produced by both KD-182-1 and KD-182-3 CAR-T cells than the cells of control groups, and suggested that KD-182-1 and KD-182-3 CAR-T cells had a good anti-tumor effect.

Example 7. In Vitro Assay for Both KD-182-1 and KD-182-3 CAR-T Cells

Figure 6:
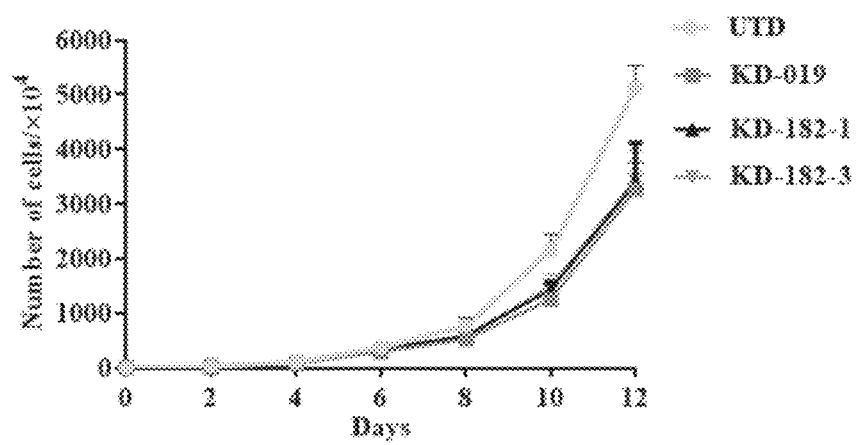
FIG. 6 shows the results of proliferation of KD-182-1 and KD-182-3 CAR-T cells in embodiment 7.

First, the KD-019, KD-182-1 and KD-182-3 CAR-T cells were prepared according to the method of Example 4 and were inoculated 24 hours after infection. After that, cells were seeded into 96-wells at a density of $4\times10^4$ cells/well on day 0, and were counted every other day. As shown in FIG. 6, the results showed that KD-182-1 and KD-182-3 CAR-T cells had a good ability to expand in vitro and the number of cells was not significantly different from control cells.

Figure 7:
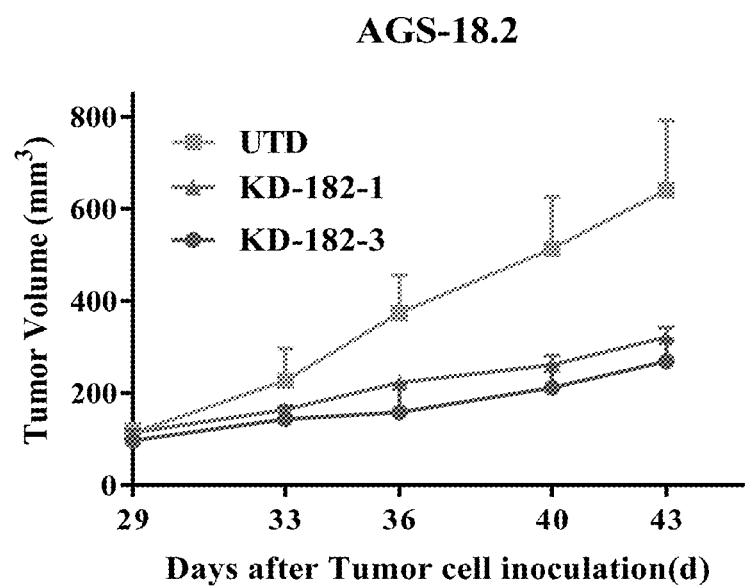
FIG. 7 depicts KD-182-1 and KD-182-3 CAR-T cells suppressed the growth of AGS-18.2 xenografts in embodiment 8.

Example 8. KD-182-1 and KD-182-3 CAR-T Cells Suppressed the Growth of AGS-18.2 Xenografts The specific procedures are as follows: AGS-18.2 cells were resuscitated and cultured. Trypan blue count showed that the viability of AGS-18.2 cells should be greater than 98%. The AGS-18.2 cells were suspended in normal saline containing 25% Matrigel (high concentration). Each mouse was subcutaneously injected with $10^6$ cells/100 μL AGS-18.2, and tumor-bearing mice with a tumor size range of 100 $mm^3$ were randomly divided into vehicle control or treatment groups (n=5). CAR-T cells were infected according to the method of Example 4, mice were treated with 100 μl of untransduced T (UTD), KD-182-1, or KD-182-3 CAR-T cells ($1\times10^8$ cells/ml) by intravenous injection. Mouse body weight and tumor volume were measured twice weekly. As shown in FIG. 7, the tumor weight in KD-182-1 and KD-182-3 CAR-T groups had a lower tumor weight compared to mice in the control group.

Figure 8A:
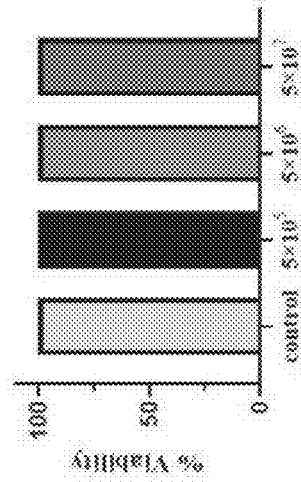
Figure 8B:
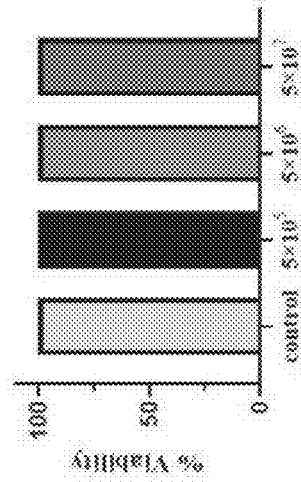
Figure 8C:
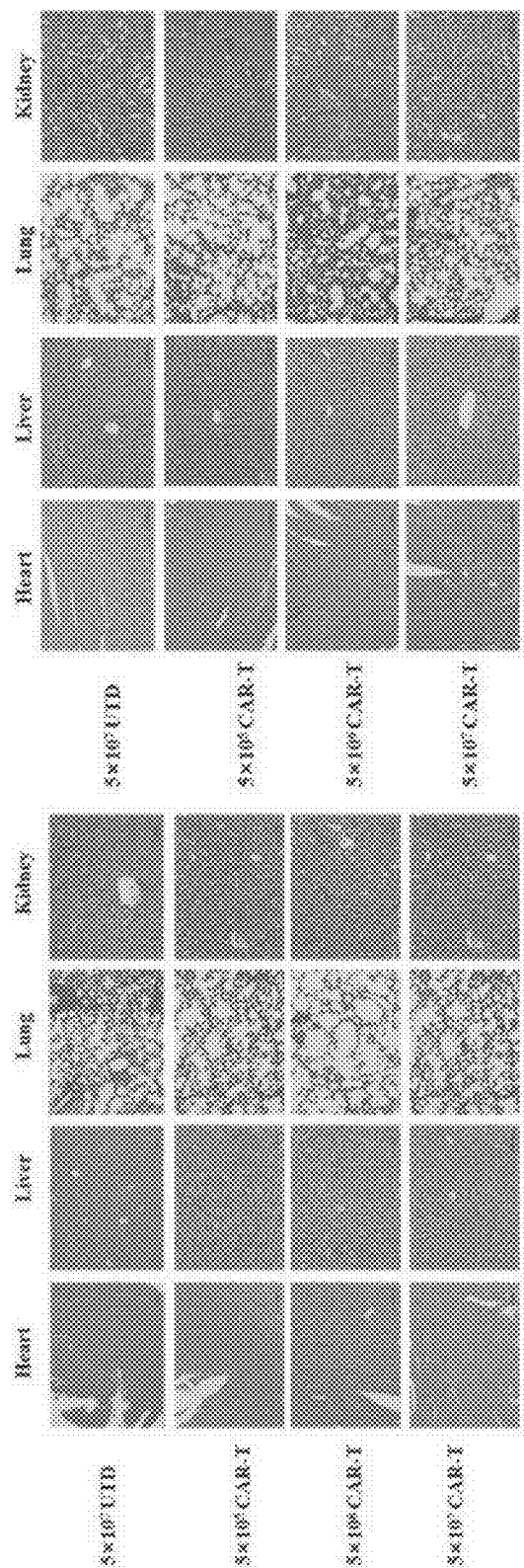
Figure 8D:
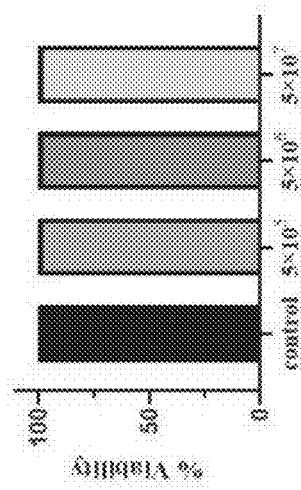

Example 9. On-target Off-tumor Toxicities of Both KD-182-1 and KD-182-3 CAR-T Cells First, the effector cells (KD-182-1 and KD-182-3 CAR-T cells) were prepared according to the method of Example 4, mice were treated with different dose of KD-182-1 or KD-182-3 CAR-T cells by intravenous injection. As shown in FIGS. 8A and 8B, KD-182-1 and KD-182-3 CAR-T cells had no significant side effect on mice. And there was no negative effect on the life cycle of the mice as shown in FIGS. 8C and 8D.

In conclusion, the viral vector or engineered immune cells which specifically target the chimeric antigen receptor of human CLDN18A2 can be applied to treat a variety of tumors, including gastric cancer, pancreatic cancer, liver cancer, brain cancer, lymph cancer, leukemia, colorectal cancer, lung cancer, or breast cancer. Furthermore, after reading the above teachings of the invention, it should be understood that those skilled in the art can make many variations or modifications to the present invention, these equivalent forms are also within the scope defined by the appended claims.

What is claimed is:

1. An immune effector cell, comprising a chimeric antigen receptor, wherein the chimeric antigen receptor is expressed on a surface of the immune effector cell, wherein the chimeric antigen receptor comprises an extracellular binding region, a transmembrane region, and an intracellular signal region, wherein the extracellular binding region comprises a protein which specifically recognizes human CLDN 18A2, and wherein the chimeric antigen receptor comprises an amino acid sequence set forth in any one of SEQ ID NOS: 13-16.

2. The immune effector cell according to claim 1, wherein the immune effector cell is selected from the group consisting of cytotoxic T lymphocytes, NK cells, NKT cells, helper T cells, and macrophages.

3. A pharmaceutical composition, comprising the immune effector cell according to claim 1.

4. A method for treating a tumor in a patient, comprising: administering the immune effector cell according to claim 1 to the patient, wherein the tumor is a CLDN18A2 positive tumor, thereby treating the tumor.

5. The method according to claim 4, wherein the immune effector cell is selected from the group consisting of cytotoxic T lymphocytes, NK cells, NKT cells, helper T cells, and macrophages.

6. A chimeric antigen receptor, comprising an extracellular binding region, a transmembrane region, and an intracellular signal region, wherein the extracellular binding region comprises a protein which specifically recognizes human CLDN 18A2, and wherein the chimeric antigen receptor comprises an amino acid sequence set forth in any one of SEQ ID NOS: 13-16.

7. A method for preparing a genetically modified immune effector cell targeting human CLDN18A2, comprising: expressing the chimeric antigen receptor according to claim 6 on a surface of the immune effector cell.

* * * * *

SEQUENCE LISTING

```
<160> NUMBER OF SEQ ID NOS: 20

<210> SEQ ID NO 1
<211> LENGTH: 21
<212> TYPE: PRT
<213> ORGANISM: Artificial Sequence
<220> FEATURE:
<223> OTHER INFORMATION: Leader sequence

<400> SEQUENCE: 1

Met Ala Leu Pro Val Thr Ala Leu Leu Leu Pro Leu Ala Leu Leu Leu
1               5                   10                  15

His Ala Ala Arg Pro
            20

<210> SEQ ID NO 2
<211> LENGTH: 246
```

```
<212> TYPE: PRT
<213> ORGANISM: Artificial Sequence
<220> FEATURE:
<223> OTHER INFORMATION: CLDN18A2 single chain

<400> SEQUENCE: 2

Asp Val Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Thr Tyr Ser Phe Pro Leu Thr Phe Gly Gln Gly Thr Lys Leu Glu Ile
            100                 105                 110

Lys Gly Gly Gly Gly Ser Gly Gly Gly Gly Ser Gly Gly Gly Gly Ser
        115                 120                 125

Asp Val Gln Leu Val Glu Ser Gly Gly Gly Leu Val Gln Pro Gly Gly
    130                 135                 140

Ser Leu Arg Leu Ser Cys Ala Ala Ser Gly Phe Thr Phe Ser Ser Phe
145                 150                 155                 160

Gly Met His Trp Val Arg Gln Ala Pro Gly Lys Gly Leu Glu Trp Val
                165                 170                 175

Ala Phe Ile Ser Ser Gly Ser His Thr Ile Tyr Tyr Ala Asp Ser Val
            180                 185                 190

Lys Gly Arg Phe Ser Ile Ser Arg Asp Asn Ala Lys Asn Thr Leu Phe
        195                 200                 205

Leu Gln Met Asn Ser Leu Arg Ala Glu Asp Thr Ala Val Tyr Tyr Cys
    210                 215                 220

Ala Arg Phe Gln Tyr Gly Asn Ser Phe Asp Tyr Trp Gly Gln Gly Thr
225                 230                 235                 240

Leu Val Thr Val Ser Ser
                245

<210> SEQ ID NO 3
<211> LENGTH: 246
<212> TYPE: PRT
<213> ORGANISM: Artificial Sequence
<220> FEATURE:
<223> OTHER INFORMATION: CLDN18A2 single chain

<400> SEQUENCE: 3

Asp Val Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Asn Ser
            20                  25                  30

Gly Asn Gln Lys Asn Tyr Leu Thr Trp Tyr Leu Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Lys
65                  70                  75                  80
```

-continued

Ile Ser Arg Val Glu Ala Glu Asp Val Gly Val Tyr Tyr Cys Gln Asn
                85                  90                  95

Thr Tyr Ser Phe Pro Leu Thr Phe Gly Gln Gly Thr Lys Leu Glu Ile
            100                 105                 110

Lys Gly Gly Gly Gly Ser Gly Gly Gly Ser Gly Gly Gly Gly Ser
        115                 120                 125

Asp Val Gln Leu Val Glu Ser Gly Gly Gly Leu Val Gln Pro Gly Gly
    130                 135                 140

Ser Leu Arg Leu Ser Cys Ala Ala Ser Gly Phe Thr Phe Ser Ser Phe
145                 150                 155                 160

Gly Met His Trp Val Arg Gln Ala Pro Gly Lys Gly Leu Glu Trp Val
            165                 170                 175

Ala Phe Ile Ser Ser Gly Ser His Thr Ile Tyr Tyr Ala Asp Ser Val
            180                 185                 190

Lys Gly Arg Phe Ser Ile Ser Arg Asp Asn Ala Lys Asn Thr Leu Phe
            195                 200                 205

Leu Gln Met Asn Ser Leu Arg Ala Glu Asp Thr Ala Val Tyr Tyr Cys
        210                 215                 220

Ala Arg Phe Gln Tyr Gly Asn Ser Phe Asp Tyr Trp Gly Gln Gly Thr
225                 230                 235                 240

Leu Val Thr Val Ser Ser
                245

<210> SEQ ID NO 4
<211> LENGTH: 246
<212> TYPE: PRT
<213> ORGANISM: Artificial Sequence
<220> FEATURE:
<223> OTHER INFORMATION: CLDN18A2 single chain

<400> SEQUENCE: 4

Asp Ile Val Ile Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Arg Asn Tyr Leu Thr Trp Tyr Gln Gln Lys Pro Gly Gln
        35                  40                  45

Pro Pro Lys Leu Leu Phe Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Ala Tyr Tyr Tyr Pro Phe Thr Phe Gly Gly Gly Thr Lys Leu Glu Ile
            100                 105                 110

Lys Gly Gly Gly Gly Ser Gly Gly Gly Gly Ser Gly Gly Gly Gly Ser
        115                 120                 125

Glu Val Gln Leu Val Glu Ser Gly Gly Gly Val Val Gln Pro Gly Gly
    130                 135                 140

Ser Leu Arg Leu Ser Cys Ala Ala Ser Gly Phe Thr Phe Ser Lys Phe
145                 150                 155                 160

Gly Met Ser Trp Val Arg Gln Ala Pro Gly Lys Arg Leu Glu Trp Val
            165                 170                 175

Ala Thr Phe Ser Ser Gly Gly Asp Tyr Thr Phe Tyr Pro Asp Ser Val
            180                 185                 190

```
Lys Gly Arg Phe Thr Ile Ser Arg Asp Asn Ser Lys Asn Thr Leu Tyr
            195                 200                 205

Leu Gln Met Asn Ser Leu Arg Ala Glu Asp Thr Ala Val Tyr Tyr Cys
    210                 215                 220

Ala Lys Leu Tyr Tyr Gly Asn Ser Met Asp Ser Trp Ser Gln Gly Leu
225                 230                 235                 240

Ser Val Thr Val Ser Ser
                245

<210> SEQ ID NO 5
<211> LENGTH: 246
<212> TYPE: PRT
<213> ORGANISM: Artificial Sequence
<220> FEATURE:
<223> OTHER INFORMATION: CLDN18A2 single chain

<400> SEQUENCE: 5

Asp Ile Val Ile Thr Gln Ser Pro Leu Ser Leu Pro Val Thr Pro Gly
1               5                   10                  15

Glu Pro Ala Ser Ile Ser Cys Lys Ser Ser Gln Ser Leu Leu Asn Ser
            20                  25                  30

Gly Asn Gln Arg Asn Tyr Leu Thr Trp Tyr Leu Gln Lys Pro Gly Gln
        35                  40                  45

Pro Pro Lys Leu Leu Phe Tyr Trp Ala Ser Thr Arg Glu Ser Gly Val
    50                  55                  60

Pro Asp Arg Phe Thr Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Asn
                85                  90                  95

Ala Tyr Tyr Tyr Pro Phe Thr Phe Gly Gly Gly Thr Lys Leu Glu Ile
            100                 105                 110

Lys Gly Gly Gly Gly Ser Gly Gly Gly Ser Gly Gly Gly Gly Ser
        115                 120                 125

Glu Val Gln Leu Leu Glu Ser Gly Gly Gly Leu Val Gln Pro Gly Gly
    130                 135                 140

Ser Leu Arg Leu Ser Cys Ala Ala Ser Gly Phe Thr Phe Ser Lys Phe
145                 150                 155                 160

Gly Met Ser Trp Val Arg Gln Ala Pro Asp Lys Arg Leu Glu Trp Val
                165                 170                 175

Ala Thr Phe Ser Ser Gly Gly Asp Tyr Thr Phe Tyr Pro Asp Ser Val
            180                 185                 190

Lys Gly Arg Phe Thr Ile Ser Arg Asp Asn Ser Lys Asn Thr Leu Tyr
        195                 200                 205

Leu Gln Met Asn Ser Leu Arg Ala Glu Asp Thr Ala Ile Tyr Tyr Cys
    210                 215                 220

Ala Lys Leu Tyr Tyr Gly Asn Ser Met Asp Ser Trp Ser Gln Gly Leu
225                 230                 235                 240

Ser Val Thr Val Ser Ser
                245

<210> SEQ ID NO 6
<211> LENGTH: 45
<212> TYPE: PRT
<213> ORGANISM: Artificial Sequence
<220> FEATURE:
<223> OTHER INFORMATION: CD8 hinge region
```

```
<400> SEQUENCE: 6

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 7
<211> LENGTH: 24
<212> TYPE: PRT
<213> ORGANISM: Artificial Sequence
<220> FEATURE:
<223> OTHER INFORMATION: CD8 transmembrane domain

<400> SEQUENCE: 7

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 8
<211> LENGTH: 27
<212> TYPE: PRT
<213> ORGANISM: Artificial Sequence
<220> FEATURE:
<223> OTHER INFORMATION: CD28 transmembrane domain

<400> SEQUENCE: 8

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 9
<211> LENGTH: 42
<212> TYPE: PRT
<213> ORGANISM: Artificial Sequence
<220> FEATURE:
<223> OTHER INFORMATION: 4-1BB endodomain

<400> SEQUENCE: 9

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 10
<211> LENGTH: 41
<212> TYPE: PRT
<213> ORGANISM: Artificial Sequence
<220> FEATURE:
<223> OTHER INFORMATION: CD28 co-stimulatory endodomain

<400> SEQUENCE: 10

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
```

35                  40

<210> SEQ ID NO 11
<211> LENGTH: 36
<212> TYPE: PRT
<213> ORGANISM: Artificial Sequence
<220> FEATURE:
<223> OTHER INFORMATION: OX40 endodomain

<400> SEQUENCE: 11

Arg Asp Gln Arg Leu Pro Pro Asp Ala His Lys Pro Pro Gly Gly Gly
1               5                   10                  15

Ser Phe Arg Thr Pro Ile Gln Glu Glu Gln Ala Asp Ala His Ser Thr
            20                  25                  30

Leu Ala Lys Ile
        35

<210> SEQ ID NO 12
<211> LENGTH: 112
<212> TYPE: PRT
<213> ORGANISM: Artificial Sequence
<220> FEATURE:
<223> OTHER INFORMATION: CD3zeta endodomain

<400> SEQUENCE: 12

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 13
<211> LENGTH: 490
<212> TYPE: PRT
<213> ORGANISM: Artificial Sequence
<220> FEATURE:
<223> OTHER INFORMATION: chimeric antigen receptor protein KD-182-1

<400> SEQUENCE: 13

Met Ala Leu Pro Val Thr Ala Leu Leu Leu Pro Leu Ala Leu Leu Leu
1               5                   10                  15

His Ala Ala Arg Pro Asp Val Val Met Thr Gln Ser Pro Asp Ser Leu
            20                  25                  30

Ala Val Ser Leu Gly Glu Arg Ala Thr Ile Asn Cys Lys Ser Ser Gln
        35                  40                  45

Ser Leu Leu Asn Ser Gly Asn Gln Lys Asn Tyr Leu Thr Trp Tyr Gln
    50                  55                  60

Gln Lys Pro Gly Gln Pro Pro Lys Leu Leu Ile Tyr Trp Ala Ser Thr
65                  70                  75                  80

Arg Glu Ser Gly Val Pro Asp Arg Phe Ser Gly Ser Gly Ser Gly Thr
                85                  90                  95

Asp Phe Thr Leu Thr Ile Ser Ser Leu Gln Ala Glu Asp Val Ala Val
                100                 105                 110

Tyr Tyr Cys Gln Asn Thr Tyr Ser Phe Pro Leu Thr Phe Gly Gln Gly
            115                 120                 125

Thr Lys Leu Glu Ile Lys Gly Gly Gly Ser Gly Gly Gly Gly Ser
    130                 135                 140

Gly Gly Gly Gly Ser Asp Val Gln Leu Val Glu Ser Gly Gly Gly Leu
145                 150                 155                 160

Val Gln Pro Gly Gly Ser Leu Arg Leu Ser Cys Ala Ala Ser Gly Phe
                165                 170                 175

Thr Phe Ser Ser Phe Gly Met His Trp Val Arg Gln Ala Pro Gly Lys
            180                 185                 190

Gly Leu Glu Trp Val Ala Phe Ile Ser Ser Gly Ser His Thr Ile Tyr
        195                 200                 205

Tyr Ala Asp Ser Val Lys Gly Arg Phe Ser Ile Ser Arg Asp Asn Ala
210                 215                 220

Lys Asn Thr Leu Phe Leu Gln Met Asn Ser Leu Arg Ala Glu Asp Thr
225                 230                 235                 240

Ala Val Tyr Tyr Cys Ala Arg Phe Gln Tyr Gly Asn Ser Phe Asp Tyr
                245                 250                 255

Trp Gly Gln Gly Thr Leu Val Thr Val Ser Ser Thr Thr Pro Ala
            260                 265                 270

Pro Arg Pro Pro Thr Pro Ala Pro Thr Ile Ala Ser Gln Pro Leu Ser
            275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490

<210> SEQ ID NO 14
<211> LENGTH: 490

```
<212> TYPE: PRT
<213> ORGANISM: Artificial Sequence
<220> FEATURE:
<223> OTHER INFORMATION: chimeric antigen receptor protein KD-182-2

<400> SEQUENCE: 14
```

| | | | | | | | | | | | | | | |
|---|---|---|---|---|---|---|---|---|---|---|---|---|---|---|
| Met | Ala | Leu | Pro | Val | Thr | Ala | Leu | Leu | Leu | Pro | Leu | Ala | Leu | Leu |
| 1 | | | | 5 | | | | | 10 | | | | | 15 |
| His | Ala | Ala | Arg | Pro | Asp | Val | Val | Met | Thr | Gln | Thr | Pro | Leu | Ser | Leu |
| | | | 20 | | | | | 25 | | | | | 30 | | |
| Ser | Val | Thr | Pro | Gly | Gln | Pro | Ala | Ser | Ile | Ser | Cys | Lys | Ser | Ser | Gln |
| | | 35 | | | | | 40 | | | | | 45 | | | |
| Ser | Leu | Leu | Asn | Ser | Gly | Asn | Gln | Lys | Asn | Tyr | Leu | Thr | Trp | Tyr | Leu |
| | 50 | | | | | 55 | | | | | 60 | | | | |
| Gln | Lys | Pro | Gly | Gln | Pro | Pro | Lys | Leu | Leu | Ile | Tyr | Trp | Ala | Ser | Thr |
| 65 | | | | | 70 | | | | | 75 | | | | | 80 |
| Arg | Glu | Ser | Gly | Val | Pro | Asp | Arg | Phe | Ser | Gly | Ser | Gly | Ser | Gly | Thr |
| | | | | 85 | | | | | 90 | | | | | 95 | |
| Asp | Phe | Thr | Leu | Lys | Ile | Ser | Arg | Val | Glu | Ala | Glu | Asp | Val | Gly | Val |
| | | | 100 | | | | | 105 | | | | | 110 | | |
| Tyr | Tyr | Cys | Gln | Asn | Thr | Tyr | Ser | Phe | Pro | Leu | Thr | Phe | Gly | Gln | Gly |
| | | 115 | | | | | 120 | | | | | 125 | | | |
| Thr | Lys | Leu | Glu | Ile | Lys | Gly | Gly | Gly | Ser | Gly | Gly | Gly | Gly | Ser |
| 130 | | | | | 135 | | | | | 140 | | | | | |
| Gly | Gly | Gly | Gly | Ser | Asp | Val | Gln | Leu | Val | Glu | Ser | Gly | Gly | Gly | Leu |
| 145 | | | | | 150 | | | | | 155 | | | | | 160 |
| Val | Gln | Pro | Gly | Gly | Ser | Leu | Arg | Leu | Ser | Cys | Ala | Ala | Ser | Gly | Phe |
| | | | 165 | | | | | 170 | | | | | 175 | | |
| Thr | Phe | Ser | Ser | Phe | Gly | Met | His | Trp | Val | Arg | Gln | Ala | Pro | Gly | Lys |
| | | | 180 | | | | | 185 | | | | | 190 | | |
| Gly | Leu | Glu | Trp | Val | Ala | Phe | Ile | Ser | Ser | Gly | Ser | His | Thr | Ile | Tyr |
| | | 195 | | | | | 200 | | | | | 205 | | | |
| Tyr | Ala | Asp | Ser | Val | Lys | Gly | Arg | Phe | Ser | Ile | Ser | Arg | Asp | Asn | Ala |
| | 210 | | | | | 215 | | | | | 220 | | | | |
| Lys | Asn | Thr | Leu | Phe | Leu | Gln | Met | Asn | Ser | Leu | Arg | Ala | Glu | Asp | Thr |
| 225 | | | | | 230 | | | | | 235 | | | | | 240 |
| Ala | Val | Tyr | Tyr | Cys | Ala | Arg | Phe | Gln | Tyr | Gly | Asn | Ser | Phe | Asp | Tyr |
| | | | | 245 | | | | | 250 | | | | | 255 | |
| Trp | Gly | Gln | Gly | Thr | Leu | Val | Thr | Val | Ser | Ser | Thr | Thr | Thr | Pro | Ala |
| | | | 260 | | | | | 265 | | | | | 270 | | |
| Pro | Arg | Pro | Pro | Thr | Pro | Ala | Pro | Thr | Ile | Ala | Ser | Gln | Pro | Leu | Ser |
| | | 275 | | | | | 280 | | | | | 285 | | | |
| Leu | Arg | Pro | Glu | Ala | Cys | Arg | Pro | Ala | Ala | Gly | Gly | Ala | Val | His | Thr |
| | 290 | | | | | 295 | | | | | 300 | | | | |
| Arg | Gly | Leu | Asp | Phe | Ala | Cys | Asp | Ile | Tyr | Ile | Trp | Ala | Pro | Leu | Ala |
| 305 | | | | | 310 | | | | | 315 | | | | | 320 |
| Gly | Thr | Cys | Gly | Val | Leu | Leu | Leu | Ser | Leu | Val | Ile | Thr | Leu | Tyr | Cys |
| | | | | 325 | | | | | 330 | | | | | 335 | |
| Lys | Arg | Gly | Arg | Lys | Lys | Leu | Leu | Tyr | Ile | Phe | Lys | Gln | Pro | Phe | Met |
| | | | 340 | | | | | 345 | | | | | 350 | | |
| Arg | Pro | Val | Gln | Thr | Thr | Gln | Glu | Glu | Asp | Gly | Cys | Ser | Cys | Arg | Phe |
| | | 355 | | | | | 360 | | | | | 365 | | | |
| Pro | Glu | Glu | Glu | Glu | Gly | Gly | Cys | Glu | Leu | Arg | Val | Lys | Phe | Ser | Arg |
| | 370 | | | | | 375 | | | | | 380 | | | | |

```
Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
            405                 410                 415

Arg Gly Arg Asp Pro Glu Met Gly Gly Lys Pro Arg Arg Lys Asn Pro
        420                 425                 430

Gln Glu Gly Leu Tyr Asn Glu Leu Gln Lys Asp Lys Met Ala Glu Ala
            435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490

<210> SEQ ID NO 15
<211> LENGTH: 490
<212> TYPE: PRT
<213> ORGANISM: Artificial Sequence
<220> FEATURE:
<223> OTHER INFORMATION: chimeric antigen receptor protein KD-182-3

<400> SEQUENCE: 15

Met Ala Leu Pro Val Thr Ala Leu Leu Leu Pro Leu Ala Leu Leu Leu
1               5                   10                  15

His Ala Ala Arg Pro Asp Ile Val Ile Thr Gln Ser Pro Asp Ser Leu
            20                  25                  30

Ala Val Ser Leu Gly Glu Arg Ala Thr Ile Asn Cys Lys Ser Ser Gln
        35                  40                  45

Ser Leu Leu Asn Ser Gly Asn Gln Arg Asn Tyr Leu Thr Trp Tyr Gln
    50                  55                  60

Gln Lys Pro Gly Gln Pro Pro Lys Leu Leu Phe Tyr Trp Ala Ser Thr
65                  70                  75                  80

Arg Glu Ser Gly Val Pro Asp Arg Phe Thr Gly Ser Gly Ser Gly Thr
                85                  90                  95

Asp Phe Thr Leu Thr Ile Ser Ser Leu Gln Ala Glu Asp Val Ala Val
            100                 105                 110

Tyr Tyr Cys Gln Asn Ala Tyr Tyr Pro Phe Thr Phe Gly Gly Gly
        115                 120                 125

Thr Lys Leu Glu Ile Lys Gly Gly Gly Ser Gly Gly Gly Gly Ser
    130                 135                 140

Gly Gly Gly Gly Ser Glu Val Gln Leu Val Glu Ser Gly Gly Gly Val
145                 150                 155                 160

Val Gln Pro Gly Gly Ser Leu Arg Leu Ser Cys Ala Ala Ser Gly Phe
                165                 170                 175

Thr Phe Ser Lys Phe Gly Met Ser Trp Val Arg Gln Ala Pro Gly Lys
            180                 185                 190

Arg Leu Glu Trp Val Ala Thr Phe Ser Ser Gly Gly Asp Tyr Thr Phe
        195                 200                 205

Tyr Pro Asp Ser Val Lys Gly Arg Phe Thr Ile Ser Arg Asp Asn Ser
    210                 215                 220

Lys Asn Thr Leu Tyr Leu Gln Met Asn Ser Leu Arg Ala Glu Asp Thr
225                 230                 235                 240

Ala Val Tyr Tyr Cys Ala Lys Leu Tyr Tyr Gly Asn Ser Met Asp Ser
                245                 250                 255
```

```
Trp Ser Gln Gly Leu Ser Val Thr Val Ser Ser Thr Thr Pro Ala
            260                 265                 270

Pro Arg Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
                340                 345                 350

Arg Pro Val Gln Thr Thr Gln Glu Glu Asp Gly Cys Ser Cys Arg Phe
                355                 360                 365

Pro Glu Glu Glu Glu Gly Gly Cys Glu Leu Arg Val Lys Phe Ser Arg
            370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
                420                 425                 430

Gln Glu Gly Leu Tyr Asn Glu Leu Gln Lys Asp Lys Met Ala Glu Ala
            435                 440                 445

Tyr Ser Glu Ile Gly Met Lys Gly Glu Arg Arg Arg Gly Lys Gly His
450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490

<210> SEQ ID NO 16
<211> LENGTH: 490
<212> TYPE: PRT
<213> ORGANISM: Artificial Sequence
<220> FEATURE:
<223> OTHER INFORMATION: chimeric antigen receptor protein KD-182-4

<400> SEQUENCE: 16

Met Ala Leu Pro Val Thr Ala Leu Leu Leu Pro Leu Ala Leu Leu Leu
1               5                   10                  15

His Ala Ala Arg Pro Asp Ile Val Ile Thr Gln Ser Pro Leu Ser Leu
                20                  25                  30

Pro Val Thr Pro Gly Glu Pro Ala Ser Ile Ser Cys Lys Ser Ser Gln
            35                  40                  45

Ser Leu Leu Asn Ser Gly Asn Gln Arg Asn Tyr Leu Thr Trp Tyr Leu
50                  55                  60

Gln Lys Pro Gly Gln Pro Pro Lys Leu Leu Phe Tyr Trp Ala Ser Thr
65                  70                  75                  80

Arg Glu Ser Gly Val Pro Asp Arg Phe Thr Gly Ser Gly Ser Gly Thr
                85                  90                  95

Asp Phe Thr Leu Lys Ile Ser Arg Val Glu Ala Glu Asp Val Gly Val
                100                 105                 110

Tyr Tyr Cys Gln Asn Ala Tyr Tyr Tyr Pro Phe Thr Phe Gly Gly Gly
            115                 120                 125
```

```
Thr Lys Leu Glu Ile Lys Gly Gly Gly Ser Gly Gly Gly Ser
    130                 135                 140

Gly Gly Gly Ser Glu Val Gln Leu Leu Glu Ser Gly Gly Leu
145                 150                 155                 160

Val Gln Pro Gly Gly Ser Leu Arg Leu Ser Cys Ala Ala Ser Gly Phe
                165                 170                 175

Thr Phe Ser Lys Phe Gly Met Ser Trp Val Arg Gln Ala Pro Asp Lys
            180                 185                 190

Arg Leu Glu Trp Val Ala Thr Phe Ser Ser Gly Gly Asp Tyr Thr Phe
                195                 200                 205

Tyr Pro Asp Ser Val Lys Gly Arg Phe Thr Ile Ser Arg Asp Asn Ser
210                 215                 220

Lys Asn Thr Leu Tyr Leu Gln Met Asn Ser Leu Arg Ala Glu Asp Thr
225                 230                 235                 240

Ala Ile Tyr Tyr Cys Ala Lys Leu Tyr Tyr Gly Asn Ser Met Asp Ser
                245                 250                 255

Trp Ser Gln Gly Leu Ser Val Thr Val Ser Ser Thr Thr Pro Ala
                260                 265                 270

Pro Arg Pro Pro Thr Pro Ala Pro Thr Ile Ala Ser Gln Pro Leu Ser
            275                 280                 285

Leu Arg Pro Glu Ala Cys Arg Pro Ala Ala Gly Gly Ala Val His Thr
290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
                340                 345                 350

Arg Pro Val Gln Thr Thr Gln Glu Glu Asp Gly Cys Ser Cys Arg Phe
            355                 360                 365

Pro Glu Glu Glu Glu Gly Gly Cys Glu Leu Arg Val Lys Phe Ser Arg
370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
                420                 425                 430

Gln Glu Gly Leu Tyr Asn Glu Leu Gln Lys Asp Lys Met Ala Glu Ala
            435                 440                 445

Tyr Ser Glu Ile Gly Met Lys Gly Glu Arg Arg Arg Gly Lys Gly His
450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490

<210> SEQ ID NO 17
<211> LENGTH: 1470
<212> TYPE: DNA
<213> ORGANISM: Artificial Sequence
<220> FEATURE:
<223> OTHER INFORMATION: chimeric antigen receptor protein KD-182-1

<400> SEQUENCE: 17
```

| | |
|---|---|
| atggccctgc cgtcaccgc tctgctgctg ccccttgctc tgcttcttca tgcagcaagg | 60 |
| ccggacgtgg tcatgacgca gtcaccggat tcactggcag taagtcttgg ggagcgagcg | 120 |
| acaatcaact gcaaatctag ccagagtctt cttaactccg gtaatcagaa gaattacttg | 180 |
| acttggtacc aacagaagcc aggacagccg cctaagcttc tgatctactg ggcgtctaca | 240 |
| cgcgagtcag gtgtacctga tcgattctcc gggagtggat ccggcacgga tttcacgctc | 300 |
| acgataagta gcttgcaagc tgaggatgtt gctgtctact attgccagaa tacatatagt | 360 |
| tttccactga cgttcggaca agggacgaag ctggaaataa aaggggtgg agggtccggc | 420 |
| ggcgggggat caggcggcgg tgggtccgat gtgcaattgg tagaatccgg tggcggtctg | 480 |
| gtacaacctg gcggatcttt gaggctgtcc tgcgccgcga gtggttttac attctcaagc | 540 |
| tttggcatgc attgggttag gcaagcccct ggtaagggtc tggagtgggt cgccttcatt | 600 |
| tcttctggaa gtcatacgat ttattacgcg gattctgtca aagggcgctt ctctatctca | 660 |
| agggataacg cgaagaatac acttttttctc caaatgaata gcttgagagc ggaggacaca | 720 |
| gccgtttatt actgcgctcg cttccagtac ggcaatagct ttgactattg ggggcaaggt | 780 |
| actttggtta ctgtctcatc taccacgacg ccagcgccgc gaccaccaac accggcgccc | 840 |
| accatcgcgt cgcagcccct gtccctgcgc ccagaggcgt gccggccagc ggcggggggc | 900 |
| gcagtgcaca cgagggggct ggacttcgcc tgtgatatct acatctgggc gcccttggcc | 960 |
| gggacttgtg gggtccttct cctgtcactg gttatcaccc tttactgcaa cggggcagaa | 1020 |
| aagaaactcc tgtatatatt caaacaacca tttatgagac cagtacaaac tactcaagag | 1080 |
| gaagatggct gtagctgccg atttccagaa gaagaagaag gaggatgtga actgagagtg | 1140 |
| aagttcagca ggagcgcaga cgcccccgcg taccagcagg gccagaacca gctctataac | 1200 |
| gagctcaatc taggacgaag agaggagtac gatgtttttgg acaagagacg tggccgggac | 1260 |
| cctgagatgg ggggaaagcc gagaaggaag aaccctcagg aaggcctgta caatgaactg | 1320 |
| cagaaagata gatggcggga ggcctacagt gagattggga tgaaaggcga cgccggagg | 1380 |
| ggcaaggggc acgatggcct ttaccagggt ctcagtacag ccaccaagga cacctacgac | 1440 |
| gcccttcaca tgcaggccct gcccctcgc | 1470 |

<210> SEQ ID NO 18
<211> LENGTH: 1470
<212> TYPE: DNA
<213> ORGANISM: Artificial Sequence
<220> FEATURE:
<223> OTHER INFORMATION: chimeric antigen receptor protein KD-182-2

<400> SEQUENCE: 18

| | |
|---|---|
| atggccctgc cgtcaccgc tctgctgctg ccccttgctc tgcttcttca tgcagcaagg | 60 |
| ccggacgtag taatgacaca aaccccgctg tctctttctg ttacgcctgg gcagcctgct | 120 |
| tccatttcat gtaaaagttc tcagagtttg ttgaatagcg ggaaccaaaa gaattatctg | 180 |
| acgtggtacc tccaaaaacc tggtcaaccg cctaaactcc tgatctactg ggccagcaca | 240 |
| cgagagtccg gcgttccaga tcgatttttcc ggaagtgggt ccgggacgga cttcaccctg | 300 |
| aagatttcaa gagtcgaagc agaggatgta gcgtgtact actgccaaaa cacatatagc | 360 |
| tttccactca catttggaca aggcactaag ctggagataa aggtggagg aggctcaggg | 420 |
| ggtggtggct ctggaggcgg gggaagcgat gttcaacttg tggagagtgg cggaggactt | 480 |
| gtgcaaccag ggggtagtct gcggctctca tgcgccgcta gtggattcac atttagctct | 540 |
| tttgggatgc attgggtgag acaagcaccc ggcaaggggc ttgaatgggt ggcatttatc | 600 |

```
agtagcggct cccatactat ttattatgcc gattccgtca agggcaggtt tagtatctca    660
cgcgataatg ctaaaaacac attgttcctg caaatgaact cactccgcgc agaagacacg    720
gcggtctatt attgcgcgcg ctttcaatac ggaaactctt tcgattactg gggtcaagga    780
acccttgtta ctgtcagctc caccacgacg ccagcgccgc gaccaccaac accggcgccc    840
accatcgcgt cgcagcccct gtccctgcgc ccagaggcgt gccggccagc ggcgggggc    900 gcagtgcaca cgagggggct ggacttcgcc tgtgatatct acatctgggc gcccttggcc    960
gggacttgtg gggtccttct cctgtcactg gttatcaccc tttactgcaa acggggcaga   1020
aagaaactcc tgtatatatt caaacaacca tttatgagac cagtacaaac tactcaagag   1080
gaagatggct gtagctgccg atttccagaa gaagaagaag gaggatgtga actgagagtg   1140
aagttcagca ggagcgcaga cgcccccgcg taccagcagg gccagaacca gctctataac   1200
gagctcaatc taggacgaag agaggagtac gatgtttggg acaagagacg tggccgggac   1260
cctgagatgg ggggaaagcc gagaaggaag aaccctcagg aaggcctgta caatgaactg   1320
cagaaagata agatggcgga ggcctacagt gagattggga tgaaaggcga gcgccggagg   1380
ggcaaggggc acgatggcct ttaccagggt ctcagtacag ccaccaagga cacctacgac   1440
gcccttcaca tgcaggccct gcccctcgc                                   1470

<210> SEQ ID NO 19
<211> LENGTH: 1470
<212> TYPE: DNA
<213> ORGANISM: Artificial Sequence
<220> FEATURE:
<223> OTHER INFORMATION: chimeric antigen receptor protein KD-182-3

<400> SEQUENCE: 19
atggccctgc ccgtcaccgc tctgctgctg ccccttgctc tgcttcttca tgcagcaagg     60
ccggatatcg ttataaccca atctcccgac tcattggcag tcagtttggg cgaacgggcg    120
actattaact gtaaatcatc acagtctttg ctcaactcag gcaatcagag aaattacctg    180
acttggtatc aacagaagcc cgggcaaccc caaaaactgt tgttttattg ggcttcaaca    240
cgggaaagtg gggtgcctga tcggtttaca gggagcggat ccggcaccga ttttactttg    300
acaatctctt cactgcaagc cgaggacgta gcggtttact attgtcaaaa tgcctattat    360
tacccattta ccttcggagg cgggacaaaa cttgaaataa agggtggcgg aggctctggc    420
ggcgggggct caggggggtgg tggttctgag gttcaacttg tagagagtgg aggaggagtt    480
gtacaaccgg gggcagtct tagctttct tgcgctgcat ctgggtttac attctctaag    540
tttggaatga gttgggtgag acaagcgccc ggtaagcgcc ttgagtgggt agcaactttt    600
agctcaggtg tgactacac cttctaccca gactccgtga agggtcggtt caccattagc    660
cgagataact caaaaaacac gctttacctg caaatgaaca gtctgcgagc tgaggatacg    720
gcggtatatt actgtgcaaa gttgtattat ggaaatagca tggattcctg gagccagggt    780
ctctctgtga cagtttctag taccacgacg ccagcgccgc gaccaccaac accggcgccc    840
accatcgcgt cgcagcccct gtccctgcgc ccagaggcgt gccggccagc ggcgggggc    900 gcagtgcaca cgagggggct ggacttcgcc tgtgatatct acatctgggc gcccttggcc    960
gggacttgtg gggtccttct cctgtcactg gttatcaccc tttactgcaa acggggcaga   1020
aagaaactcc tgtatatatt caaacaacca tttatgagac cagtacaaac tactcaagag   1080
gaagatggct gtagctgccg atttccagaa gaagaagaag gaggatgtga actgagagtg   1140
```

```
aagttcagca ggagcgcaga cgcccccgcg taccagcagg gccagaacca gctctataac    1200
gagctcaatc taggacgaag agaggagtac gatgttttgg acaagagacg tggccgggac    1260
cctgagatgg ggggaaagcc gagaaggaag aaccctcagg aaggcctgta caatgaactg    1320
cagaaagata gatggcggga ggcctacagt gagattggga tgaaaggcga gcgccggagg    1380
ggcaaggggc acgatggcct ttaccagggt ctcagtacag ccaccaagga cacctacgac    1440
gcccttcaca tgcaggccct gccccctcgc                                      1470

<210> SEQ ID NO 20
<211> LENGTH: 1470
<212> TYPE: DNA
<213> ORGANISM: Artificial Sequence
<220> FEATURE:
<223> OTHER INFORMATION: chimeric antigen receptor protein KD-182-4

<400> SEQUENCE: 20
atggccctgc ccgtcaccgc tctgctgctg ccccttgctc tgcttcttca tgcagcaagg      60
ccggacatag tcataacaca atctccgctt agcttgccgg tcactcctgg cgaaccagcc    120
tctatcagtt gtaaaagctc acaatcactg ctcaatagcg aaaccagcg gaactatttg     180 acatggtacc tccaaaaacc tggtcaacct ccaaagctgc tgttttactg ggcctcaacg    240
cgggagtcag gggttcctga tcggtttact ggttcaggca gcgtacagat tttacgctg     300 aaaataagca gggttgaggc agaagatgtc ggtgtctatt actgtcagaa cgcatattac    360
tacccgttta cctttggtgg cggtacaaag ctggaaatca aggcggggg cggaagcgga    420 ggtggtggtt caggtggagg cggttccgaa gtgcagcttc ttgaaagtgg tggtgggttg    480
gtacaaccag gaggcagtct cagactgtcc tgtgccgctt ccggcttcac gttctctaag    540
tttggaatgt catgggtacg acaggcaccc gataagcgcc tcgaatgggt cgcaactttt    600
tccagcggtg gtgattacac gttctatcca gattcagtca aaggccggtt tacgatctcc    660
cgagataaca gtaagaatac actgtatctt caaatgaatt cacttcgggc agaagatacc    720
gcgatttatt attgcgctaa actttactac gggaactcta tggattcctg gagtcaaggc    780
ttgagtgtta ctgtatcaag taccacgacg ccagcgccgc gaccaccaac accggcgccc    840
accatcgcgt cgcagcccct gtccctgcgc ccagaggcgt gccggccagc ggcggggggc    900
gcagtgcaca cgagggggct ggacttcgcc tgtgatatct acatctgggc gcccttggcc    960
gggacttgtg ggtccttct cctgtcactg gttatcaccc tttactgcaa cgggcaga     1020 aagaaactcc tgtatatatt caaacaacca tttatgagac cagtacaaac tactcaagag    1080
gaagatggct gtagctgccg atttccagaa gaagaagaag aggatgtgaa ctgagagtg    1140 aagttcagca ggagcgcaga cgcccccgcg taccagcagg gccagaacca gctctataac    1200
gagctcaatc taggacgaag agaggagtac gatgttttgg acaagagacg tggccgggac    1260
cctgagatgg ggggaaagcc gagaaggaag aaccctcagg aaggcctgta caatgaactg    1320
cagaaagata gatggcggga ggcctacagt gagattggga tgaaaggcga gcgccggagg    1380
ggcaaggggc acgatggcct ttaccagggt ctcagtacag ccaccaagga cacctacgac    1440
gcccttcaca tgcaggccct gccccctcgc                                      1470
```